(12) United States Patent
Nelson (10) Patent No.: US 6,770,893 B2
(45) Date of Patent: Aug. 3, 2004

(54) METHOD AND APPARATUS FOR EMISSION COMPUTED TOMOGRAPHY USING TEMPORAL SIGNATURES

(75) Inventor: Alan C. Nelson, Gig Harbor, WA (US)

(73) Assignee: Visiongate, Inc., Gig Harbor, WA (US)

( * ) Notice: Subject to any disclaimer, the term of this patent is extended or adjusted under 35 U.S.C. 154(b) by 178 days.

(21) Appl. No.: 10/147,154

(22) Filed: May 13, 2002

(65) Prior Publication Data

US 2003/0210760 A1 Nov. 13, 2003

(51) Int. Cl.⁷ .............................................. G01N 21/84
(52) U.S. Cl. .................. 250/458.1; 600/425; 250/459.1
(58) Field of Search ............................ 378/4, 8, 21, 44; 382/133, 134; 250/455.11, 461.2, 363.04, 363.05, 459.1, 458.1, 461.1; 600/425, 769, 317

(56) References Cited

U.S. PATENT DOCUMENTS

| | | |
|---|---|---|
| 3,470,373 A | 9/1969 | Brewer |
| 3,497,690 A | 2/1970 | Wheeless, Jr. |
| 3,598,471 A | 8/1971 | Baldwin |
| 3,657,537 A | 4/1972 | Wheeless, Jr. |
| 3,748,468 A | 7/1973 | Hartman |
| 3,833,762 A | 9/1974 | Gudmundsen |
| 3,960,449 A | 6/1976 | Carlton |
| 3,999,047 A | 12/1976 | Green |
| 4,175,860 A | 11/1979 | Bacus |
| 4,200,353 A | 4/1980 | Hoffman |
| 4,293,221 A * | 10/1981 | Kay et al. .................. 356/318 |
| 4,360,885 A | 11/1982 | Edgar |
| 4,873,653 A | 10/1989 | Grosskopf |
| 5,141,609 A | 8/1992 | Sweedler et al. |
| 5,148,502 A | 9/1992 | Tsujiuchi et al. |
| 5,281,517 A | 1/1994 | Bacus et al. |
| 5,308,990 A | 5/1994 | Takahashi et al. |
| 5,312,535 A | 5/1994 | Waska et al. |
| 5,402,460 A | 3/1995 | Johnson |
| 5,668,887 A | 9/1997 | Parker et al. |
| 5,680,484 A | 10/1997 | Ohyama et al. |
| 5,710,429 A | 1/1998 | Alfano et al. |
| 5,741,411 A | 4/1998 | Yeung et al. |
| 5,828,408 A | 10/1998 | Mottin et al. |
| 5,848,123 A | 12/1998 | Strommer |
| 5,878,103 A | 3/1999 | Sauer et al. |

(List continued on next page.)

OTHER PUBLICATIONS

Ong et al., Development of an imaging flow cytometer. Anal Quant Cytol Histol 9(5) pp. 375–382. 1987.*

Shapiro, HM, *Practical Flow Cytometry*, 3rd ed., Wiley-Liss, 1995.

(List continued on next page.)

*Primary Examiner*—Edward J. Glick
*Assistant Examiner*—Hoon Song
(74) *Attorney, Agent, or Firm*—George A. Leone (57) ABSTRACT

An optical tomographic system wherein the localization of secondary emitters within an object of interest is determined using the temporal signatures of secondary emission arising from the object being illuminated by an external primary source beam that is non-parallel, such as a cone beam, while the object is moving relative to said beam in a controlled manner. A unique set of secondary emitter spots is localized within the object and, when combined with a computed 3D reconstruction of the object from its primary cone beam projections, creates an image of the secondary emitters in the object so as to enable quantitative three-dimensional imaging of fluorescent labeled molecular probes in a biological cell, for example.

20 Claims, 8 Drawing Sheets

U.S. PATENT DOCUMENTS

| | | | |
|---|---|---|---|
| 5,880,838 | A | 3/1999 | Marx et al. |
| 5,909,476 | A | 6/1999 | Cheng et al. |
| 5,987,158 | A | 11/1999 | Meyer |
| 6,005,617 | A | 12/1999 | Shimamoto et al. |
| 6,026,174 | A | 2/2000 | Palcic |
| 6,047,080 | A | 4/2000 | Chen et al. |
| 6,091,983 | A | 7/2000 | Alfano et al. |
| 6,130,958 | A | 10/2000 | Rohler et al. |
| 6,165,734 | A | 12/2000 | Garini |
| 6,201,628 | B1 | 3/2001 | Basiji |
| 6,211,955 | B1 | 4/2001 | Basiji |
| 6,215,587 | B1 | 4/2001 | Alfano et al. |
| 6,226,352 | B1 | 5/2001 | Salb |
| 6,248,988 | B1 | 6/2001 | Krantz |
| 6,249,341 | B1 | 6/2001 | Basiji |
| 6,251,586 | B1 | 6/2001 | Mulshine |
| 6,251,615 | B1 | 6/2001 | Oberhardt |
| 6,252,979 | B1 | 6/2001 | Lee |
| 6,452,179 | B1 | 9/2002 | Coates et al. |
| 6,529,614 | B1 | 3/2003 | Chao et al. |
| 2001/0012069 | A1 | 8/2001 | Derndinger et al. |
| 2002/0161534 | A1 | 10/2002 | Adler et al. |

OTHER PUBLICATIONS

Gilbert, P. "Iterative Methods for the Three dimensional Reconstruction of an Object from Projections," Journal of Theoretical Biology 36:105–17, 1972.

Oppenheim, BE, More Accurate Algorithms for Iterative 3 dimensional Reconstruction, IEEE Transactions on Nuclear Science NS–21:72–7, 1974.

Singer, JR, Grunbaum, FA, Kohn, P, and Zubelli, JP, "Image Reconstruction of the Interior of Bodies that Diffuse Radiation," Science 248(4958):990–3, 1990.

Mueller, K and Yage, R, "Rapid 3–D Cone–beam Reconstruction with the Simultaneous Algebraic Reconstruction Technique (SART) Using 2–D Texture Mapping Hardware", IEEE Transactions on Medical imaging 19(12):1227–37, 2001.

Bellman, SH, Bender, R, Gordon, R, and Rowe, JE, "ART is Science being A Defense of Algebraic Reconstruction Techniques for Three dimensional Electron Microscopy," Journal of Theoretical Biology 32:205–16, 1971.

Manglos, SH, Jaszcak, RJ, and Floyd, CE, "Maximum Likelihood Reconstruction for Cone Beam SPECT: Development and Initial Tests," Physics in Medicine and Biology 34(12):1947–57, 1989, #1382.

Manglos, SH, Gagne, GM, Krol A, Thomas, FD, and Narayanaswamy, R, "Transmission Maximum–likelihood Reconstruction with Ordered Subsets for Cone Beam CT", Physics in Medicine and Biology 40(7):1225–41, 1995, #4389.

Hampel, U and Freyer, R, "Fast Image Reconstruction for Optical Absorption Tomography in Media with Radially Symmetric Boundaries", Medical Physics 25 (1):92–101, 1998.

Jiang, H. Paulsen, KD, and Osterberg, UL, "Frequency–domain Near–infrared Photo Diffusion Imaging: Initial Evaluation in Multitarget Tissuelike Phantoms", Medical Physics 25(2):183–93, 1998.

Herman, G, *Image Reconstruction from Projections: The Fundamentals of Computerized Tomography*, Academic Press, New York, 1980.

Paulsen, KD and Jiang, H, "Spatially Varying Optical Property Reconstruction Using a Finite Element Diffusion Equation Approximation", Medical Physics 22(691–701) 1995.

Ong, SH, Development of an imaging flow cytometer. Anal Quant Cytol Histol 9(5)pp. 375–382, 1987.

Kikuchi, S. et al., "Three–dimensional computed tomography for optical microscopes," Optics Communications 107 (1994) 432–444.

Kikuchi, S. et al., "Three–dimensional microscopic computed tomography based on general Radon transform for optical imaging systems," Optics Communicatons 123 (1996).

Matula, P. et al. "Precise 3D image alignment in micro–axial tomography," Journal of Microscopy, vol. 209, Pt. 2 (Feb. 2003) pp. 126–142.

Farichild Imaging, Preliminary Data Sheet CCD525, TDI, Time Delay and Integration Sensor, Jan. 12, 2001.

Farichild Imaging, Preliminary Data Sheet CCD582, TDI, Time Delay and INtegration Sensor, Jan. 18, 2000.

Bayat, S, Le Duc, G, Porra, L, Berrruyer, G, Nemoz, C, Monfraix, S, Fiedler, S, Thomlinson, W, Suortti, P, Standertskjold–Nordenstam, CG, and Sovijarvi, ARA, "Quantitative Functional Lung Imaging with Synchrotron Radiation Using Inhaled Xenon as Contrast Agent", Physics in Medicine and Biology 46(3287–99) 2001.

Bentley, MD, Ortiz, MC, Ritman, EL, and Romero, JC, "The Use of Microcomputed Tomography to Study Microvasculature in Small Rodents", American Journal of Physiology (Regulatory Integrative Comp Physiol) 282(R1267–R1279) 2002.

Cheng, PC, Lin, TH, Wang, G, Shinozaki, DM, Kim, HG, and Newberry, SP, "Review on the Development of Cone–beam X–ray Microtomography", Proceedings of the X–ray Optics and Microanalysis 1992, Institute of Physics Ser. No. 130, Kenway, PB, et al. (eds.).

Defrise, M, Clack, R, and Townsend, DW, "Image Reconstruction from Truncated, Two–dimensional, Parallel Projections", Inverse Problems 11(287–313) 1995.

Defrise, M, Noo, F, and Kudo, H, "A Solution to the Long–object Problem in Helical Cone–beam Tomography", Physics in Medicine and Biology 45(623–43) 2000.

Endo, M, Tsunoo, T, Nakamori, N, and Yoshida, K, "Effect of Scattered Radiation on Image Noise on Cone Beam CT", Medical Physics 28(4) (469–74) 2001.

Jorgensen, SM, Demirkaya, O, and Ritman, EL, "Three Dimensional Imaging of Vasculature and Parenchyma in Intact Rodent Organs with X–ray Micro–CT", Am. J. Physiology 275(Heart Circ. Physiol. 44) pp. H1103–14, 1998.

Kinney, JH, Johnson, QC, Saroyan, RA, Nichols, MC, Bonse, U, Nusshardt, R, and Pahl, R, "Energy–modulated X–ray Microtomography", Rev. Sci. Instrum. 59(1)pp. 196–197, 1988.

Kinney, JH and Nichols, MC, "X–ray Tomographic Microscopy (XTM) Using Synchrotron Ratiation", Annu. Rev. Mater. Sci. 22pp. 121–152, 1992.

Taguchi, K and Aradate, H, "Algorithm for Image Reconstruction in Multi–slice Helical CT", Medical Physics 25(4)pp. 550–561, 1998.

Yu, DF, Fessler, JA, and Ficaro, EP, "Maximum–Likelihood Transmission Image Reconstruction for Overlapping Transmission Beams", IEEE Transactions on Medical Imaging 19(11)pp. 1094–1105, 2000.

* cited by examiner

METHOD AND APPARATUS FOR EMISSION COMPUTED TOMOGRAPHY USING TEMPORAL SIGNATURES

FIELD OF THE INVENTION

The present invention relates to optical tomography systems in general, and more particularly to those tomography systems that utilize an illumination system comprised of photon beams wherein each beam consists of photons that are not parallel, such as a cone beam or a fan beam for illuminating fluorescent molecular probes.

BACKGROUND OF THE INVENTION

The use of molecular probes in the analysis of biological cells has illuminated many aspects of the disease process in cells. Molecular probes are used in several applications, and those tagged with fluorescent molecules have been particularly useful. However, it has not been possible to combine highly quantitative measurements of the amount of bound probes within a cell with the precise three-dimensional (3D) localization of these probes within subcellular structures.

U.S. application Ser. No. 09/927,151 of Alan C. Nelson, filed Aug. 10, 2001, entitled "APPARATUS AND METHOD FOR IMAGING SMALL OBJECTS IN A FLOW STREAM USING OPTICAL TOMOGRAPHY," and U.S. application Ser. No. 10/126,026 of Alan C. Nelson, filed Aug. 19, 2002, entitled "VARIABLE-MOTION OPTICAL TOMOGRAPHY OF SMALL OBJECTS" (hereinafter called the FOT and VOT systems, respectively, or the optical tomography systems (OT systems), taken together) are both incorporated herein by this reference. In the aforesaid Nelson patent applications, OT systems are described that utilize divergent optical beams, such as a cone beam or a fan beam, in geometries that facilitate the 3D computed image reconstruction of small objects such as biological cells. As input to reconstruction algorithms, these OT systems generate a set of projection images, also called shadowgrams that are generated by detecting absorption of photons from the primary beam by an object of interest. Unfortunately, the OT systems do not address the additional case where molecules within the object of interest emit secondary photons when illuminated by the primary beam, and hence, a new methodology is required to compute the 3D arrangement of these probes through emission computed tomography.

Localizing sources of emission from within an object of interest, a cell for example, has been a significant challenge to the scientific community. Those skilled in the art will recognize that even current solutions are inadequate, including the use of collimation at the detector to determine the solid angle direction of detected photons and the use of precise time-of-flight measurements to track the distance from the detector to the emission source.

SUMMARY OF THE INVENTION

In one embodiment, the present invention provides a method for emission computed tomography (ECT). In accordance with one example of the present invention, the relative motion of an object of interest, such as a cell, through a non-parallel beam, such as a cone beam or a fan beam, where the cell has been exposed to molecular probes that can fluoresce while passing through the beam, generates temporal signatures. The temporal signatures are combined with a tomographic reconstruction from projections to generate an accurate 3D image of the fluorescent tagged subcellular structures. Using the temporal signatures of objects tagged with fluorescent molecules moving relative to such beams in conjunction with tomographic reconstruction from projections, the fluorescent signals are accurately measured and localized.

In the case of tomographic image reconstruction from projections, the present invention overcomes the drawbacks of the prior art by, for the first time, advantageously using the reconstructed image in conjunction with measurements of emission from within the cell to pinpoint the location of internal emission sources. One example of the method of the invention employs non-parallel primary beams, such as cone beams or fan beams, which are divergent beams, coupled with relative motion between the beam and the cell to generate a set of temporal signatures that are mapped into the cell through a combination of hyperbolic surfaces and pattern matching to uniquely localize the emission sources within the reconstructed cell image.

DETAILED DESCRIPTION OF THE PREFERRED EMBODIMENTS

Figure 1:
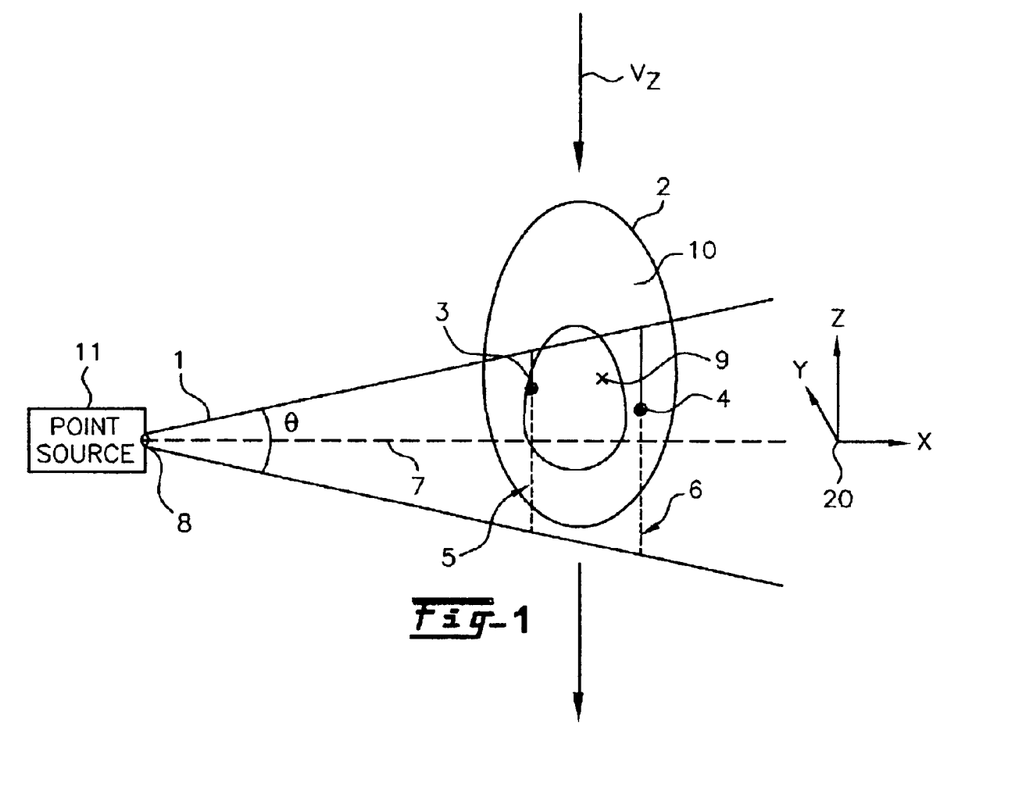
FIG. 1 schematically shows an example illustration of a cone beam with a cell moving relative to the beam with velocity vector ($V_z$) and containing a first spot and a second spot, the spots representing fluorescent labeled molecular probes whose locations generate different path lengths due to different distances along a central axis from a cone apex whose solid angle is θ.

Referring now to FIG. 1, an example illustration of a cone beam of illumination 1, as viewed substantially perpendicularly into the plane of the paper, with a cell 2 moving relative to the beam with a known constant velocity vector ($V_z$) and including a first spot 3 and a second spot 4 is schematically shown. The first spot 3 and the second spot 4 represent fluorescent labeled molecular probes having locations that generate different path lengths 5 and 6, respectively; due to different distances along a central axis 7 from a cone apex 8 whose solid angle is θ. In the example, the first spot 3 is located in the cell nucleus 9, and the second spot 4 is located in the cell cytoplasm 10. The central axis 7 may conveniently be related to a conventional coordinate system 20 including X and Z axes for defining coordinates.

The cone beam 1 illuminates the first spot 3 over a shorter duration than the second spot 4 because of the first spot's relatively shorter distance from the apex 8 of the cone. In the simple planar view of FIG. 1, the positions of the first spot and the second spot can be precisely mapped when the velocity vector of the cell (and any structure within the cell) is known, the position of the cell is known and the duration of illumination of each spot is known. The latter measurement can be made, for example, when the spots are bound with fluorescent tagged molecular probes that fluoresce under exposure to the cone beam 1 used as a primary light source.

Light Source

In a preferred embodiment, the cone beam 1 is a light beam generated by a point source 11. Each source may have the same general characteristics, preferably:

it may approximate a small circular point source for use in cone beam geometry, it may be bright, uniform and with known spectral content, and the photons emitted from the source may have a known geometry such as a cone beam or a fan beam.

Further, the wavelength of the point sources is selectable either by use of various diode emitters, other lasers or by bandpass filtering of a white or other broadband source, such as, for example, a mercury or xenon arc lamp.

There are several options that can be employed to create optical point sources, such as:

a pinhole in front of a laser or other high intensity photon source, an optical fiber with a small cross-section and small apparent aperture, a short focal length lens in front of a photon source, an electron beam that irradiates a point on a phosphor surface (a form of CRT), and various combinations of the above.

The geometry is such that, because an object closer to the source subtends a wider geometric angle, the closer the point source is to the object of interest (e.g. a cell), the higher the magnification. Magnification in a simple projection system is approximately M=(A+B)/A, where A is the distance between the point source and the object and B is the distance between the object and the detector. Conversely, if the required resolution is known in advance of the system design, then the geometry can be optimized for that particular resolution. For background, those skilled in the art are directed to Blass, M., editor-in-chief, *Handbook of Optics: Fiber Optics and Nonlinear Optics*, 2$^{nd}$ ed., Vol. IV, Mcgraw-Hill, 2001.

Figure 2A:
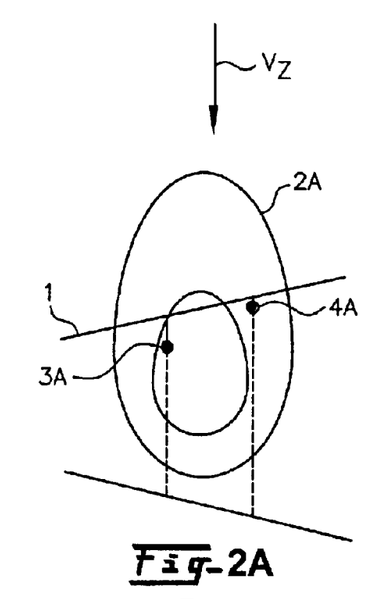
FIGS. 2A–2C illustrate examples of sets of spots representing fluorescent labeled molecular probes whose locations generate different path lengths along a central axis from a cone apex whose solid angle is θ, where the spots are located in various positions with respect to each other.
Figure 2B:
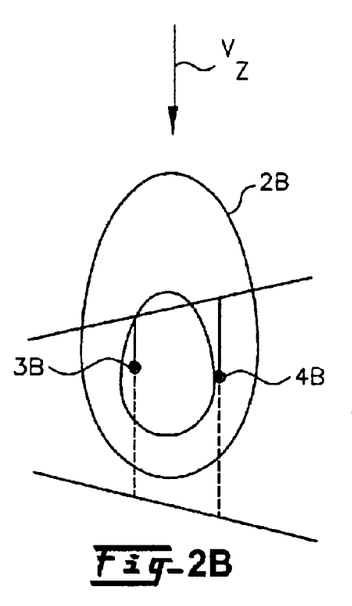
Figure 2C:
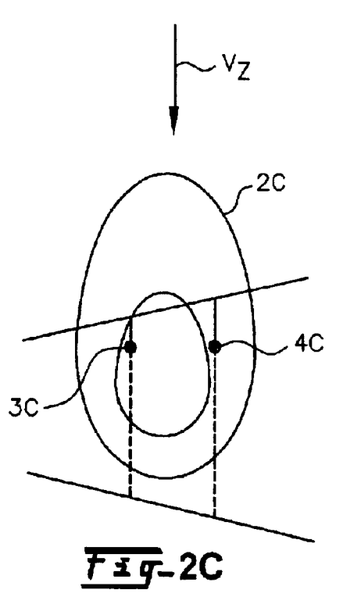

Referring now to FIGS. 2A–2C, examples of sets of spots representing fluorescent labeled molecular probes whose locations generate different path lengths along a central axis from a cone apex whose solid angle is θ, where the spots are located in various positions with respect to each other are illustrated.

FIG. 2A shows an example where a first spot 3A is hypothetically located on a portion of the cell 2 that is proximate the apex 8 (as shown in FIG. 1) relative to a second spot 4A hypothetically located on a more distant portion of the cell 2 with respect to the apex 8. As such, the first spot 3A enters the cone beam of illumination and begins fluorescing at a time before the second spot 4A enters. The first spot 3A also exits the cone beam of illumination and stops fluorescing at a time before the second spot 4A exits.

FIG. 2B shows an example where a first spot 3B is hypothetically located on a portion of the cell 2 that is proximate the apex 8 (as shown in FIG. 1) relative to a second spot 4B hypothetically located on a more distant portion of the cell 2 with respect to the apex 8. As such, the first spot 3B enters the cone beam of illumination and begins fluorescing at a time after the second spot 4B enters. The first spot 3B also exits the cone beam of illumination and stops fluorescing at a time after the second spot 4B exits.

FIG. 2C shows an example where a first spot 3C is hypothetically located on a portion of the cell 2 that is proximate the apex 8 (as shown in FIG. 1) relative to a second spot 4C hypothetically located on a more distant portion of the cell 2 with respect to the apex 8. As such, the first spot 3C enters the cone beam of illumination and begins fluorescing at a time after the second spot 4C enters. The first spot 3C also exits the cone beam of illumination and stops fluorescing at a time before the second spot 4C exits.

Figure 2D:
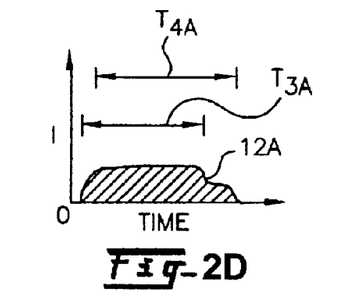
FIGS. 2D–2F illustrate examples of signal outputs showing types of temporal signatures that arise when sets of spots are in different positions.
Figure 2E:
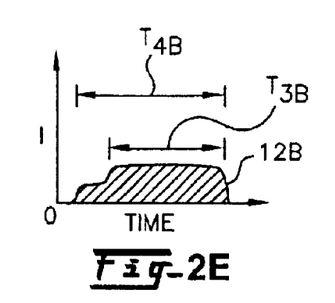
Figure 2F:
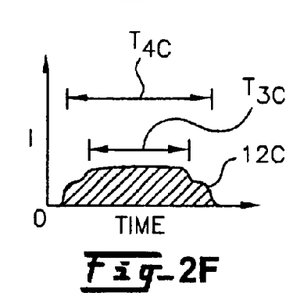

As described further hereinbelow with respect to FIG. 5, a detector, such as a filtered photomultiplier tube (PMT), that is filtered to receive only the secondary fluorescent photons, may advantageously be used as a sensor to measure the signal called temporal signatures 12A, 12B and 12C of fluorescence intensity, I, vs. time of the types shown in FIGS. 2D–2F. The signal profiles substantially correspond to signals produced by the examples of FIGS. 2A–2C respectively. The temporal signatures 12A, 12B and 12C represent an integrated measure of the unique path lengths of each spot through the cone beam in a relationship that may be expressed according to the following formula:

$$\text{Path Lengths}_s = VT_s, \tag{1}$$

where V is the velocity of the moving cell and T is the duration of the fluorescent signal from an individual spot (s). The distance of a given spot from the apex of the cone along the X-axis as a function of cone angle (θ) and the Path Length may be expressed as:

$$X_s = VT_s/2 \tan(\theta/2). \tag{2}$$

Those skilled in the art having the benefit of this disclosure will recognize that temporal signatures for cells with many fluorescent spots will become complex and that, in theory, the Fourier transform of the temporal signature will give rise to the various durations of each of the spots. Also, if the position of the cell is known as a function of time, then the beginning or ending points of duration permit the spot to be mapped to its correct location within the cell along the Z-axis. In this simple planar example, knowing the X and Z coordinates defines the unique location of the spot in the X, Z-plane of an image of the cell.

Referring again to FIG. 2D, line $T_{3A}$ corresponds to a duration measure of the time that the first spot 3A remains within the cone beam. Similarly, line $T_{4A}$ corresponds to a duration measure of the time that the second spot 4A remains within the cone beam. The durations may be derived from the temporal signature 12A wherein an increased intensity corresponds to the presence of fluorescence and a drop in intensity corresponds to a decrease in fluorescence as the spots move through the cone beam. Lines $T_{3B}$ and $T_{3C}$ similarly show first spot durations for the examples of FIGS. 2B and 2C. Lines $T_{4B}$ and $T_{4C}$ similarly show second spot durations for the examples of FIGS. 2B and 2C.

From the two-dimensional example above, it is evident that each spot has a unique path length, and, therefore, a unique distance along the X-axis can be calculated. However, in the three-dimensional case of a cone beam, the path lengths are no longer unique with the one exception of the longest path length of a spot located the furthest distance from the apex of the cone. In the three-dimensional case, there is an infinite number of all other equal length paths spread out into the Y-axis.

Figure 3:
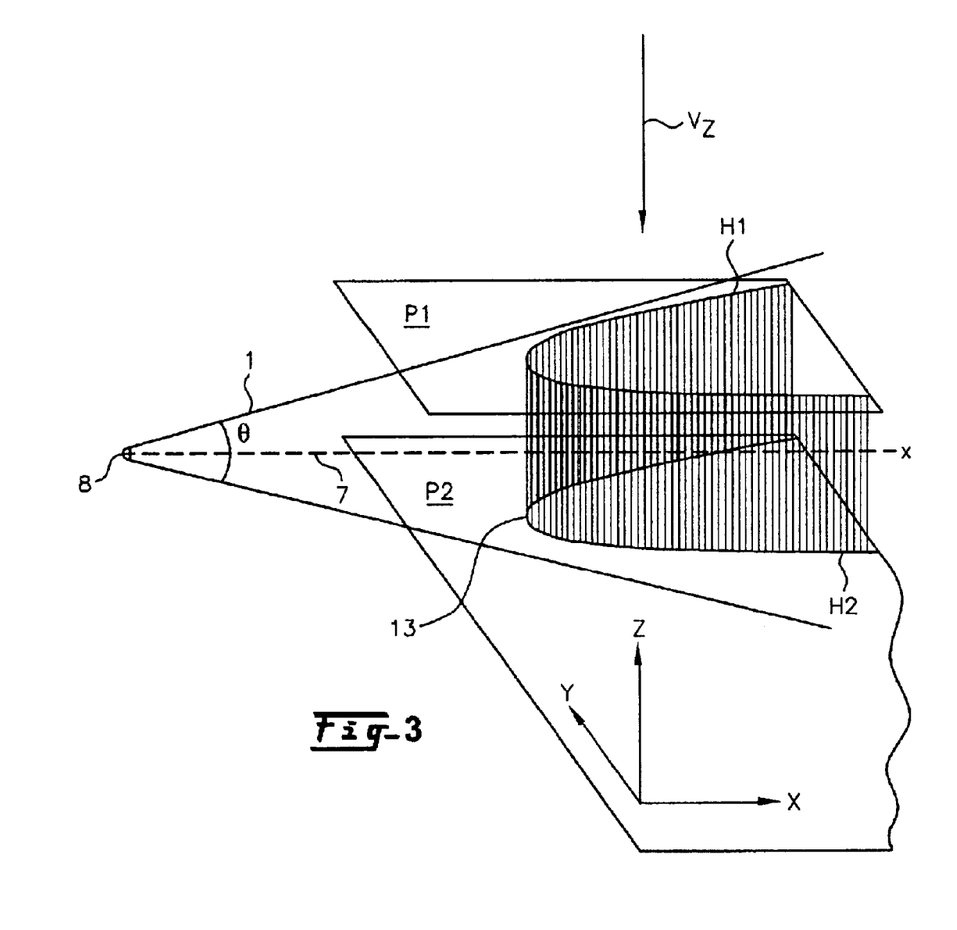
FIG. 3 schematically shows an example illustration of the hyperbolic ribbons that define the possible locations of a spot moving relative to a beam, where location corresponds to duration of the spot in the beam.

Now referring to FIG. 3, an example illustration of hyperbolic ribbons that define possible locations of a spot moving relative to a beam, where each location corresponds to a duration of the spot in the beam, is shown. From the theory of conical sections, a plane that intersects a cone parallel to the central axis of the cone describes a hyperbola. Two parallel planes P1, P2 that are also parallel to the central axis 7 of the cone beam 1, such that the cone axis 7 is equidistant between the two parallel planes P1, P2, describe two identical hyperbolas H1, H2. A surface 13 connecting the two parallel planes P1, P2, bounded by the two identical hyperbolas H1, H2 is called a hyperbolic ribbon of constant width (or path length), namely the spacing between the two planes. In cone beam geometry, when the cell is moving along a velocity vector that is perpendicular to a pair of planes, then the duration of a spot defines the distance between the two planes and the spot could lie anywhere along the corresponding hyperbolic ribbon. In other words, each unique duration yields a unique hyperbolic curve with an infinite set of equal length paths defined by the hyperbolic ribbon. In the aforesaid example, planes P1, P2 lie in parallel planes related to X, Y coordinates conventionally perpendicular to the Z dimension, and the Z distance between the planes defines the width of the hyperbolic ribbon 13.

Figure 4:
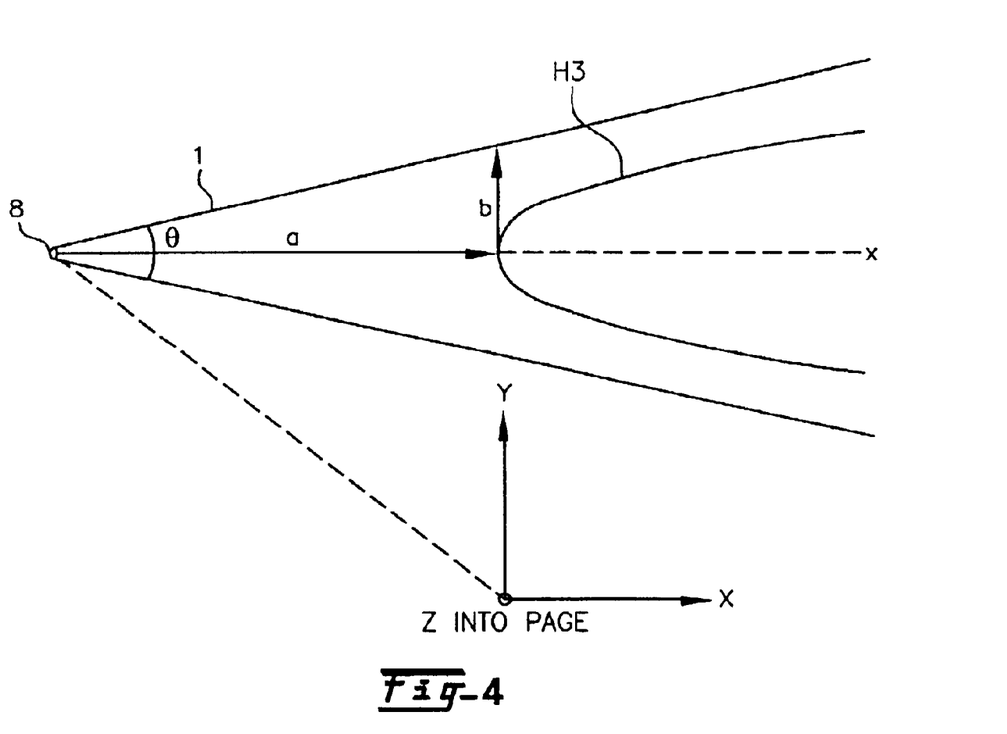
FIG. 4 schematically shows a view along the Z-axis of a hyperbola in an X, Y-plane where (a) is the distance from the point source to the inflection point of the hyperbola and (b) is the half radius on the cone beam at the distance (a).

Referring now to FIG. 4, a view into the page along the Z-axis, of a hyperbola H3 in the X, Y-plane, where (a) is the distance from the point source to the inflection point of the hyperbola and (b) is the half radius on the cone beam at the distance (a) is shown schematically. Hyperbola H3 represents one of a plurality of parallel hyperbolas contained within the hyperbolic ribbon. Each of the plurality of hyperbolas has a point closest to the apex 8 at distance (a) along the X-axis. The apex 8 may be taken as an origin for purposes of determining coordinates. The hyperbolic curve is symmetric along the Y-axis and may be advantageously defined by the following equation:

$$1 = X^2/a^2 - Y^2/b^2 \text{ and,} \quad (3)$$

$$a = b\tan(\theta/2), \text{ where } \theta \text{ is the solid angle of the cone.} \quad (4)$$

Note that b is the radius of the circular cross section of the cone beam at the inflection point of the hyperbola and is therefore equal to half the path length as defined in equation (1) above, $$b = VT/2. \quad (5)$$

Now substituting equations (4) and (5) into equation (3) and solving for X yields, $$X = 0.5 \tan(\theta/2)(V^2T^2 + 4Y^2)^{1/2}. \quad (6)$$

Again, in a cone beam optical tomography system, the solid angle $\theta$ of the cone is known, the velocity V of the cell is known, the duration T of the fluorescent spot in the cone beam is measured, and therefore, X and Y are defined by equation (6). In this geometry, X is always positive, Y is always symmetric about the X-axis and larger cone angles $\theta$ will improve the discrimination in determining the coordinates.

Figure 5:
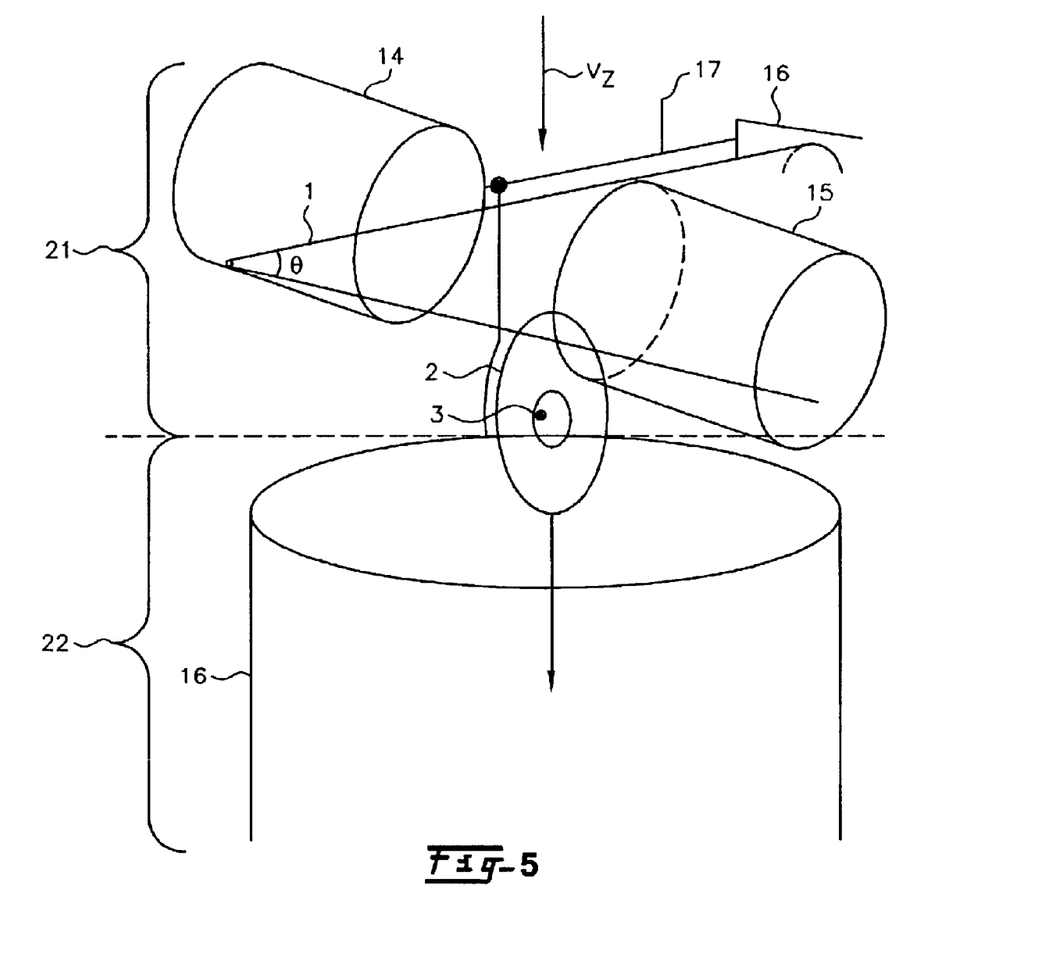
FIG. 5 schematically illustrates an example of an emission computed tomography reconstruction cylinder with an arrangement of opposed PMT emission detectors.

Referring now to FIG. 5, an example of the emission computed tomography reconstruction cylinder with an arrangement of opposed photomultiplier tube (PMT) emission detectors is schematically illustrated. A cone beam 1 is used to stimulate fluorescence. The cone beam 1 is separate from those contained in a reconstruction cylinder and as such may remain on continuously during the secondary emission process. The first and second opposed PMTs 14, 15 are filtered to receive only the secondary fluorescent photons in conjunction with the tomographic reconstruction cylinder 16. The first and second opposed PMTs 14, 15 each provide an output signal. As explained in further detail herein, the output signals are used to determine whether the Y coordinate is positive or negative and to measure the magnitude of the Y coordinate. The sum of the two PMT output signals is an estimate of the fluorescent intensity of the spot, while subtracting the two PMT output signals from each other yields the sign of the Y coordinate and an estimate of the value of Y. When Y is measured in this manner, then X is determined through equation (6). Since Z is determined by the known position of the cell as a function of time, then the X, Y, Z coordinates of the spot are now determined uniquely. Additionally, by placing a detector 16 at the distant base of the cone beam, a trigger signal 17 will be generated when the cell moves into view. The trigger signal is used to clock the position of the cell and preserve the timing between the emission signal collection cylinder 21 and the OT system 22 including a reconstruction cylinder 16 so that the two data sets will be registered in the Z-direction.

Note that since the secondary photons from the fluorescent spot are emitted radially in all directions, the measured intensity falls off as $R^3$ where R is the distance radius from the spot to the detector surface. The difference signal can be made more or less sensitive by decreasing or increasing, respectively, the solid angle of detection that is a function of the spacing between the two PMTs and their detection surface area. The configuration that works best for the difference measurement is not necessarily the best for the sum measurement and will need to be optimized based on the signal/noise considerations. Also, because any detector can be interfaced to a specific bandpass filter, then different fluorescent wavelength probes can be used simultaneously to assess the presence of several different molecular structures.

Figure 6:
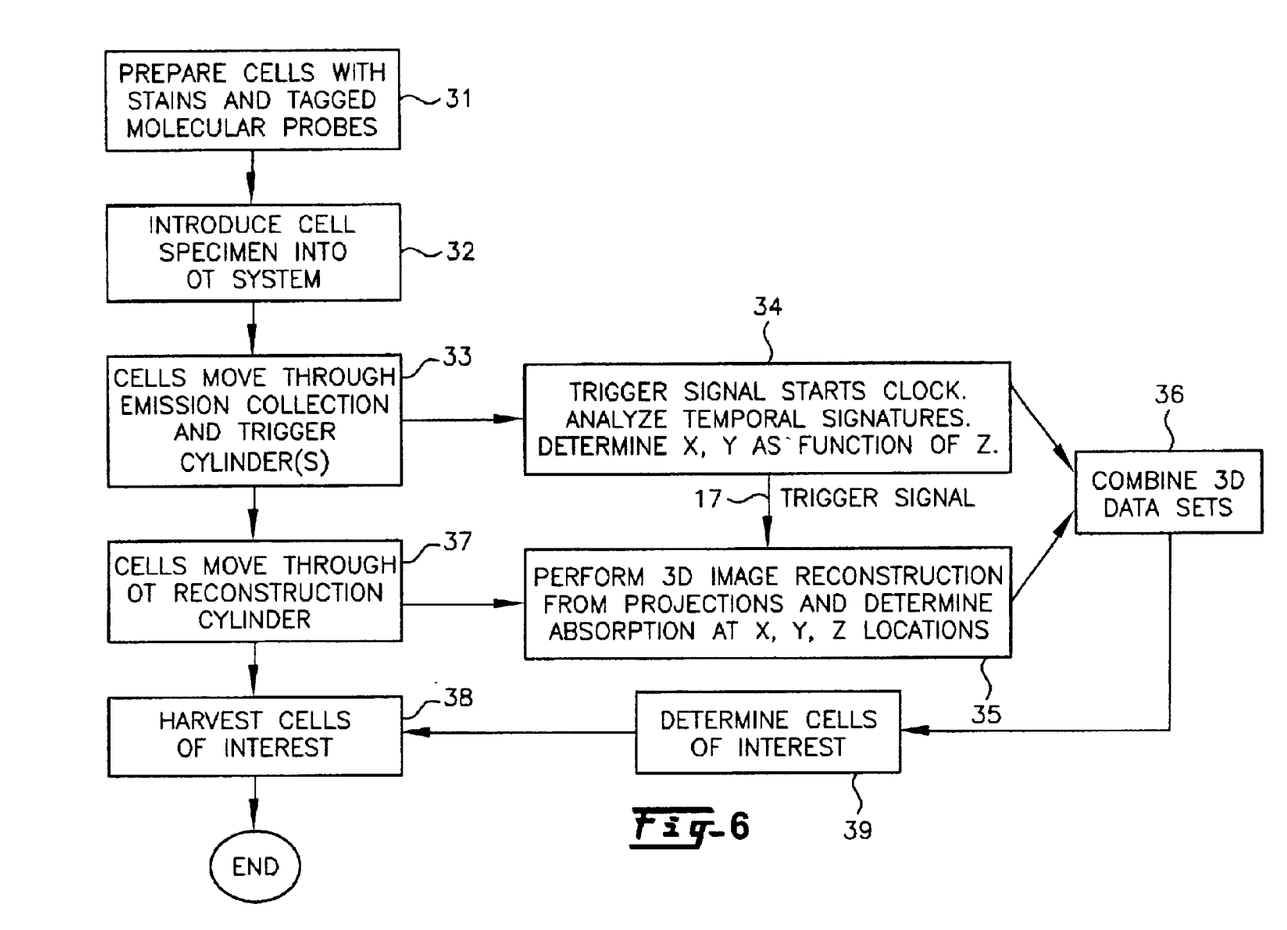
FIG. 6 schematically shows an example of the process whereby emission temporal signatures are combined with tomographic reconstruction from projections to localize fluorescent signal spots.
Figure 7:
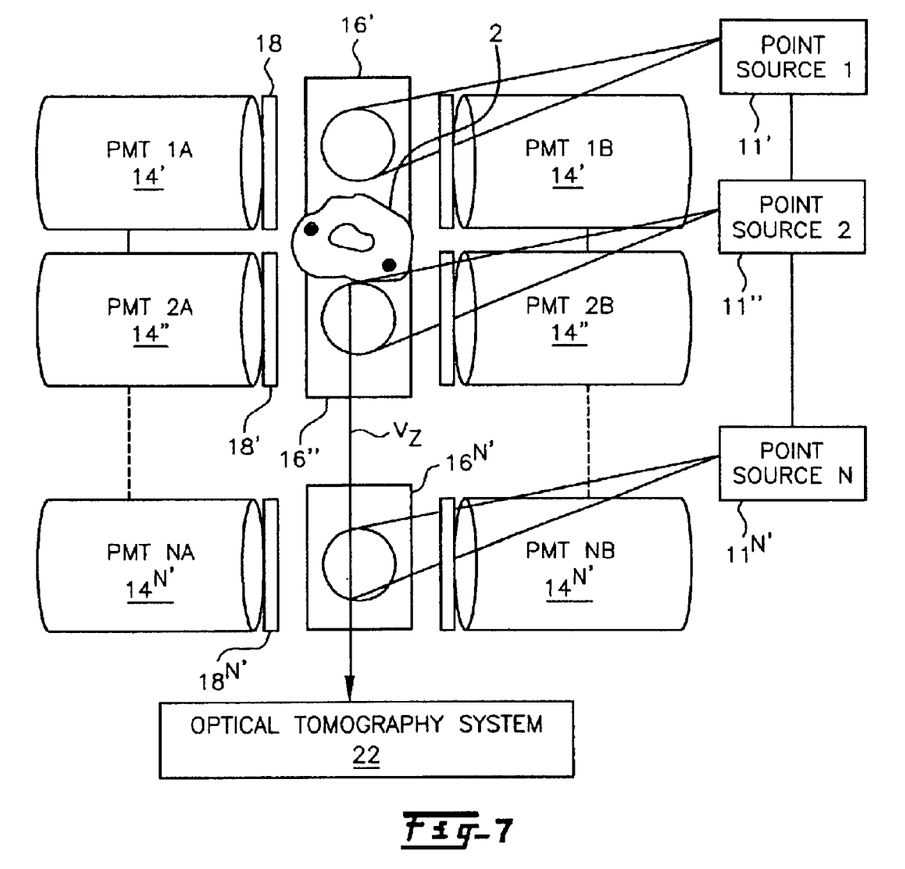
FIG. 7 schematically shows an example of an optical tomography system whereby multiple emission temporal signatures are combined with tomographic reconstruction from projections to localize fluorescent signal spots constructed in accordance with the present invention.

FIG. 6 shows a logic flow of one example of a process carried out in accordance with the method of the present invention. At step 31, cells are prepared with stains and tagged fluorescent molecular probes. At step 32, the stained/tagged cells are introduced into an optical tomography system. At step 33, the cells move through an emission collection and trigger cylinder or a plurality of emission collection and trigger cylinders as shown in FIG. 7. At step 34, the trigger signal starts clocking processes for analyzing temporal signatures and determining X, Y coordinate locations as a function of the Z coordinate of detected fluorescence of the molecular probes. At step 37 cells move through the reconstruction cylinder or OT system where substantially simultaneously the trigger signal 17 has activated the collection of shadowgrams that are input to computer processes for performing 3D reconstruction and determining absorption at X, Y and Z locations. At step 36 the 3D data sets from the temporal signature analysis and the 3D reconstruction are combined to determine cells of interest at step 39. Finally, cells of interest may be harvested at step 38.

The step of combining the data sets at step 36 comprises superposition of data sets. Because timing and positioning of cells is controlled by the OT system 22, a data set from the secondary emission mapping system 21 may advantageously be superimposed on a 3D reconstructed image of the cell to map detected fluorescent structures into the higher resolution absorption image of the cell. A high quality true 3D picture of the cell with its specific internal structures identified by fluorescent tagged molecular probes is thereby generated. A detector, such as is shown in FIG. 5 at the distant base of the cone beam is utilized to generate the trigger signal 17 that controls the timing of the image reconstruction such that the emission image and the 3D tomographic image are in register in the Z-direction and superimposed. This process simply requires the maintenance of Z-axis registration, because the X, Y-axes are spatially invariant in the design of the OT system. The known velocity of the moving cell and timing signals defines the Z-axis. Each fluorescent component in the temporal signature can be analyzed statistically to define the Z-coordinate that would be utilized in assigning a particular fluorescent spot to its respective plane in the 3D reconstructed image. Furthermore, since the process of generating secondary emission requires the absorption of primary photons in the first place, a fluorescent spot localized by the secondary emission detection system may be mapped to an absorption spot in the 3D reconstructed image. When the detectors in the reconstruction cylinder have been filtered to block out the secondary emission photons, then the contrast resolution of the reconstructed 3D absorption image will be improved, providing more statistical weight. This provides an opportunity to align fluorescent spots with absorption spots that may not exactly coincide in the superimposed data sets. A conventional analysis of sources of positioning error can be used to provide a statistical distribution of probabilities around each spot, and to find the statistically optimal fit of the two data sets.

Referring now to FIG. 7, an alternative embodiment of the invention is schematically shown including a plurality of PMTs arranged in opposing pairs. The plurality of PMTs $14'-14^{N'}$ are configured with independent cone beams $1'-1^{N'}$ using a selection of light sources $11'-11^{N'}$ and/or filters 18 are arranged along a path traveled by cell 2 having constant velocity vector $V_z$ allowing multiple wavelength source and collection combinations by the plurality of PMT devices. In this manner, it is possible to assess several (i.e. preferably more than two) different probes within the same cell. In a preferred embodiment, the cell 2 continues its travel into an optical tomography system 22 where a 3D image may be analyzed. Those skilled in the art will recognize that the system is coordinated by timing signals generated by detectors $16'-16^{N'}$. One example of a useful triggering mechanism is described in the Nelson FOT patent application. Each pair of PMTs provides outputs for localizing emission temporal signatures corresponding to the different filter wavelengths that be advantageously combined with the tomographic reconstruction of the cell using the optical tomography system 22. The plurality of sets of PMTs and associated devices may advantageously correspond to the number of wavelengths (and correspondingly different tagged probes) selected for analysis.

Figure 8:
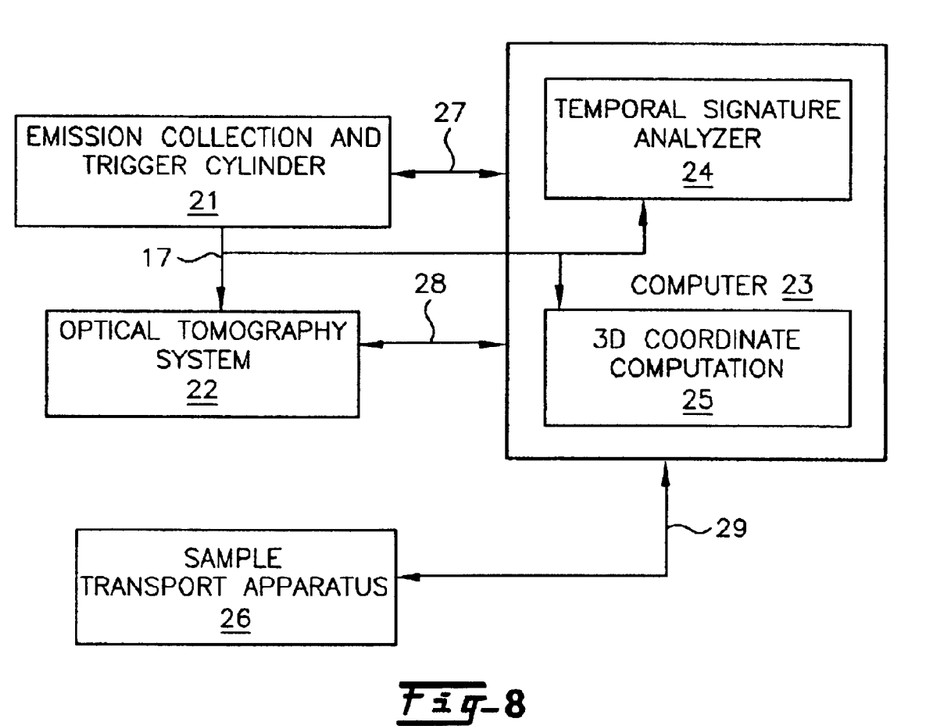
FIG. 8 schematically shows a high level block diagram of an example of an optical tomography system whereby emission temporal signatures are combined with tomographic reconstruction from projections to localize fluorescent signal spots constructed in accordance with the present invention.

Now referring to FIG. 8, a high level block diagram of an example of an optical tomography system whereby emission temporal signatures are combined with tomographic reconstruction from projections to localize fluorescent signal spots constructed in accordance with the present invention is schematically shown. The optical tomography system includes an emission collection and trigger cylinder 21, a computer 23, an optical tomography system 22 and a sample transport apparatus 26. The computer 23 includes computer software comprising a temporal signature analyzer computer algorithm 24 and a 3D coordinate computation algorithm 25. The trigger signal 17 is provided by a detector in the emission collection and trigger cylinder 21 and clocks the OT system 22, and the computer algorithms. The computer 23 communicates with and controls the emission collection and trigger cylinder 21 via communication link 28. Similarly, the computer 23 communicates with and controls the OT system via communication link 27. The sample transport apparatus 26 may be an apparatus such as is described in the Nelson FOT or VOT applications, for example, or any equivalents. The computer 23 controls and communicates with the sample transport apparatus 26 via communication link 29. The computer may be any conventional computer, such as a personal computer or an equivalent. The computer algorithms may also be carried out by equivalent means such as dedicated electronic circuits or the like or other equivalent means.

The computer 23 includes computer software modules including a temporal signature analyzer 24 and a 3D coordinate computation module. The temporal signature analyzer 24 operates to determine spot locations as described hereinabove. The 3D coordinate computation module determines X, Y and Z coordinates as described hereinabove. It will be recognized that the temporal signature analyzer and the 3D coordinate computation module may also be carried out by equivalent means such as dedicated electronic circuits, array processors, or the like or other equivalent means.

In order to promote better understanding of the invention, a description of the operation of the invention in one example embodiment follows. Beginning with the tomographic reconstruction from projections, the invention uses, for example, an optical tomography system such as a Flow Optical Tomographic system (FOT system) or a Variable Motion Optical Tomographic system (VOT system) as described in the Nelson patent applications referred to above. However, it will be understood that example descriptions herein referring to such FOT and VOT systems are for illustrative purposes only and, that such descriptions do not limit the broader application of the method to other imaging systems. Also, for illustrative purposes, an optical tomography system more particularly utilizing a cone beam will be discussed to demonstrate the emission computed tomography (ECT) method. Those skilled in the art having the benefit of this disclosure will understand that a full range of equivalent light sources may also be employed.

The cone beam optical tomography system will reconstruct the 3D image of a cell from its multiple projections (shadowgrams) to form a 3D picture where contrast is a function of the reduction of photons from the primary cone beam(s) due to absorption, scatter, diffraction or any other process that disrupts the flight of a photon from the source to the detector. If a primary photon is absorbed by a fluorescent molecular structure within the cell, which then emits another secondary photon of longer wavelength, this process will create both a contrast event in the projection shadowgram and an emission event with a secondary photon shifted to a longer wavelength. Thus, when shadowgrams are input to the image reconstruction algorithm, the absorption of primary photons by fluorescent molecules will combine with all other absorption events to create contrast variations in the shadowgrams and consequently in the reconstructed 3D image.

Image Reconstruction

The most common and easily implemented reconstruction algorithms, known as filtered backprojection methods, are derived from a similar paradigm in computerized x-ray tomography (CT) using cone-beam and fan-beam geometry. (See the following references, for example, Kak, A. C. and Slaney, M., *Principles of Computerized Tomographic Imaging*, IEEE Press, New York, 1988, and Herman, G., *Image Reconstruction from Projections: The Fundamentals of Computerized Tomography*, Academic Press, New York, 1980.) These methods are based on theorems for Radon transforms with modifications that reflect the particular geometry of the source/detector configuration and the ray paths in the irradiating beam. However, in the case of clinical x-ray CT, a human subject is usually held motionless while an x-ray source and detector arrays may move along an arc or helix around the patient to collect data from multiple projection angles. Then the human subject may be repositioned along the z-axis and another set of data is collected, etc. Alternatively, in the more modern clinical helical CT, the patient may be continuously translated in the z-direction while the source-detector assembly rotates continuously to provide helical projection data, which is then interpolated to provide projections orthogonal to the patient z-axis.

In flow optical tomography (FOT) and variable-motion optical tomography (VOT), the object (for example, a cell) is moved relative to the stationary sources and detector arrays wherein the plurality of source/detector systems acquire data in synchrony with specific gated time points along the object velocity vector in a fashion that generates multiple projection angle data within a given slice or volume. For slice-by-slice scanning using a fan beam, the reconstruction algorithm will compute a 2D image of a plane perpendicular to the axis of motion, and the serial stacking of multiple slices will generate the 3D picture of the object where contrast is a function of the variations in the x-ray attenuation coefficient or optical absorption coefficient as a measure of density within the object for CT or flow optical tomography, respectively. For volumetric, cone-beam scanning the reconstruction algorithm computes a 3D image of a volume within the cell or other object directly from planar transmission or emission optical projections, where the contrast is a function of the optical density and/or tagged probe density distribution within the imaged object.

It may be desirable for either the transmission data to produce the cell density reconstruction or for the emission data (from internal sources, if any) to reconstruct the labeled probe distribution, or both, to employ image reconstruction algorithms other than filtered backprojection. The general class known as iterative reconstruction algorithms is more efficacious in some instances, especially for emission tomography or, when it is possible, as in the instance of the current invention where the axial symmetry and tricompartmental nature of the object are known, to incorporate a priori information into the reconstruction algorithm to improve the quality of the reconstruction (See, for example, Gilbert, P., "Iterative Methods for the Three-dimensional Reconstruction of an Object from Projections," Journal of Theoretical Biology 36:105–17, 1972, and other references noted hereinabove).

Because fluorescent emissions occur in a different band of the spectrum, this property can be used advantageously in conjunction with optical filters to separate the primary photons from the emission signals. In ECT, the first 3D image reconstruction from projections is performed in the standard manner. Additionally, preferable two, but at least one, highly sensitive detectors, such as photomultiplier tubes, are positioned with a geometry that does not interfere with the source/detector geometry of the optical tomography system but allows for optimal signal collection of the emission signals. Typically, the photomultiplier tubes may advantageously be filtered to collect only the emission signals and reject the primary photons. This can be accomplished with a narrow bandpass filter and the careful selection of fluorescent molecules whose absorption spectrum minimally overlaps with its emission spectrum. In this configuration, fluorescence will occur only when the fluorescent molecules are exposed to the primary beam. If the cell containing the fluorescent molecules is moving through the primary beam with a known velocity profile, then the duration of any particular fluorescent signal will also be known and will equal the duration of that fluorescent molecule in the primary beam. Moreover, when the primary beam is a cone beam, the fluorescent signal will have a longer or shorter duration depending on the location of the fluorescent molecule further or closer, respectively, to the primary point source. The set of temporal emission signals that arise due to the passage of the cell through the cone beam and the variable distances within the conical illumination due to the location of the fluorescent molecules within the cell are called temporal signatures. These temporal signatures can be deconvolved using signal processing techniques, such as Fourier analysis, to generate a form of histogram of intensity vs. time (duration). This collection of transformed data can be translated into a distance histogram because the velocity profile of the cell moving through the cone beam is known.

The invention has been described herein in considerable detail in order to comply with the Patent Statutes and to provide those skilled in the art with the information needed to apply the novel principles of the present invention, and to construct and use such exemplary and specialized components as are required. However, it is to be understood that the invention may be carried out by specifically different equipment, and devices and reconstruction algorithms, and that various modifications, both as to the equipment details and operating procedures, may be accomplished without departing from the true spirit and scope of the present invention.

What is claimed is:

1. An emission computed tomography system comprising:

means for illuminating a plurality of secondary emitters within an object of interest by using an external non-parallel source beam while the object of interest is moving relative to said external non-parallel source beam;

means, coupled to receive radiation emitted from the plurality of secondary emitters, for providing a localization signal representing the emitted radiation;

means, coupled to receive the localization signal, for, determining a location for each of the plurality of secondary emitters;

means for producing a 3D reconstruction of the object of interest; and means for combining the location with a computed 3D reconstruction of the object of interest so as to create an image of the plurality of secondary emitters.

2. The emission computed tomography system of claim 1 wherein the object of interest comprises a biological cell.

3. The emission computed tomography system of claim 1 wherein the plurality of secondary emitters comprise a plurality of fluorescent probes.

4. The emission computed tomography system of claim 1 wherein the external non-parallel source beam comprises a cone beam.

5. The emission computed tomography system of claim 3 wherein the means for providing a localization signal comprises:
- at least one photomultiplier tube filtered to receive only the secondary fluorescent photons; and
- a detector connected to provide a trigger signal to the location determining means and the 3D reconstruction means, where the detector is located at a distant base of the cone beam and the trigger signal is produced when the cone beam is interrupted by the passage of an object of interest between the cone beam and the detector.

6. The emission computed tomography system of claim 1 wherein the radiation emitted from the plurality of secondary emitters comprises a plurality of temporal signatures; and the means for determining a location includes means for analyzing the temporal signals so as to determine the location for each of the plurality of secondary emitters.

7. The emission computed tomography system of claim 6 wherein the plurality of temporal signatures represent durations proportional to the distance that the plurality of secondary emitters travel through the external non-parallel source beam.

8. The emission computed tomography system of claim 7 wherein the velocity vector along a Z-axis of the object of interest is known and where the localization signal includes the positions of plurality of secondary emitters mapped along the Z-axis, so that Fourier transforms of the plurality of temporal signatures provide a representation of each duration of each of the plurality of secondary emitters, thereby permitting each of the plurality of secondary emitters to be mapped to its location within the object of interest along the Z-axis.

9. The emission computed tomography system of claim 8 wherein the localization signal includes location data and the means for combining comprises means for superposition of the location data with a 3D reconstructed image of the object of interest so as to map detected fluorescent structures into a higher resolution absorption image.

10. The emission computed tomography system of claim 1 wherein the means for combining further includes means for combining temporal signatures with tomographic reconstruction images from projections to localize fluorescent signal spots.

11. An optical tomography system comprises:
- an emission collection and trigger cylinder that provides a trigger signal indicating the presence of an object;
- a 3D optical tomography image reconstruction system;
- a sample transport apparatus; and
- a computer coupled to control and communicate with the emission collection and trigger cylinder, the 3D optical tomography image reconstruction system, and the sample transport apparatus where the trigger signal clocks the 3D optical tomography image reconstruction system and the computer so as to identify objects of interest.

12. The optical tomography system of claim 11 wherein the emission collection and trigger cylinder further comprises at least two opposed filtered photomultiplier tubes operating for emission collection and at least one detector for providing the trigger signal.

13. A method for emission computed tomography using temporal signatures comprising the steps of:
- preparing cells with stains and tagged fluorescent molecular probes;
- introducing the cells into an optical tomography system including an emission collection and trigger cylinder and an image reconstruction cylinder;
- moving the cells through an emission collection and trigger cylinder, where the emission collection and trigger cylinder produces a trigger signal in response to a cell entering the emission collection and trigger cylinder and wherein the cells are illuminated to produce secondary emissions;
- sensing the secondary emissions to produce a set of temporal signatures;
- using the trigger signal to start clocking processes for analyzing the set of temporal signatures and determining a first set of 3D data including X, Y coordinate locations as a function of a Z coordinate of detected fluorescence of the molecular probes;
- using the trigger signal to activate computer processes for performing 3D reconstruction of the cell structure from projections and determining absorption at X, Y and Z locations so as to generate a second set of 3D data;
- combining the first set of 3D data and the second set of 3D data to determine cells of interest;
- moving cells through the reconstruction cylinder; and
- identifying cells of interest.

14. The method of claim 13 wherein the step of combining the 3D data sets further comprises the steps of superposition of the sets of temporal signals from the secondary emission mapping system on a 3D reconstructed image of the cell to map detected fluorescent structures into a higher resolution absorption image of the cell.

15. An emission computed tomography system comprising:
- a point source for illuminating a plurality of fluorescent molecular probes within a cell, where the cell is moving relative to the point source, and where the plurality of fluorescent molecular probes fluoresce to provide emitted radiation when illuminated;
- a set of photomultiplier tubes, coupled to receive radiation emitted from at least one of the plurality of fluorescent molecular probes, for providing a temporal signature responsive to the emitted radiation for at least one of the plurality of fluorescent molecular probes;
- a temporal signal analyzer, coupled to receive the temporal signature, for determining a location for at least one of the plurality of fluorescent molecular probes;
- an optical tomography system for producing a 3D reconstruction of the cell;
- a detector connected to provide a trigger signal to synchronize the temporal signal analyzer and the optical tomography system, where the detector is located at a distant base of the cone beam and the trigger signal is produced when the cone beam is interrupted by the passage of an object of interest between the cone beam and the detector; and
- a 3D coordinate computation module for combining the location with a computed 3D reconstruction of the object of interest so as to create an image of the plurality of fluorescent molecular probes.

16. The emission computed tomography system of claim 15 wherein the point source produces a cone beam for illumination.

17. The emission computed tomography system of claim 15 wherein the set of photomultiplier tubes comprise a plurality of opposing pairs of photomultiplier tubes.

18. The emission computed tomography system of claim 17 wherein each opposing pair of photomultiplier tubes receives radiation through an optical filter passing a different preselected wavelength of radiation.

19. The optical tomography system of claim 15 wherein the 3D coordinate computation module comprises a computer software program.

20. The optical tomography system of claim 15 wherein the cell has a known velocity profile and wherein the temporal signal analyzer deconvolves temporal signatures using Fourier analysis, so as to generate a relationship of intensity vs. time.

* * * * *